(12) United States Patent
Coupard et al.

(10) Patent No.: US 6,281,402 B1
(45) Date of Patent: Aug. 28, 2001

(54) ALTERNATED PROCESS FOR OLEFIN METATHESIS

(75) Inventors: Vincent Coupard, Lyons; François Hugues, Vernaison; Dominique Commereuc, Meudon; Béatrice Fischer, Rueil Malmaison; Pierre Boucot, Ternay; Alain Forestiere, Vernaison, all of (FR)

(73) Assignee: Institut Francais du Petrole (FR)

( * ) Notice: Subject to any disclaimer, the term of this patent is extended or adjusted under 35 U.S.C. 154(b) by 0 days.

(21) Appl. No.: 09/208,585

(22) Filed: Dec. 10, 1998

(30) Foreign Application Priority Data

Dec. 10, 1997 (FR) .................................................. 97 15743

(51) Int. Cl.$^7$ ...................................................... C07C 6/04
(52) U.S. Cl. ........................ 585/644; 585/643; 585/646; 585/647
(58) Field of Search .................................. 585/643, 644, 585/646, 647

(56) References Cited

U.S. PATENT DOCUMENTS

| | | | | |
|---|---|---|---|---|
| 3,261,879 | * | 7/1966 | Banks .................................... | 585/643 |
| 3,365,512 | * | 1/1968 | Wilson et al. ........................ | 585/634 |
| 3,365,513 | * | 1/1968 | Heckelsberg ......................... | 585/643 |
| 3,676,520 | * | 7/1972 | Heckelsberg ......................... | 585/647 |
| 4,072,629 | * | 2/1978 | Jansen ..................................... | 502/30 |
| 5,336,393 | * | 8/1994 | Takatsu et al. .................. | 208/120.15 |
| 5,491,277 | * | 2/1996 | Stine et al. ............................ | 585/719 |

FOREIGN PATENT DOCUMENTS

| | | |
|---|---|---|
| 298872 | 8/1954 | (CH) . |
| 1199407 | 12/1959 | (FR) . |
| 2608595 | 12/1986 | (FR) . |

* cited by examiner

Primary Examiner—Walter D. Griffin
(74) Attorney, Agent, or Firm—Millen, White, Zelano & Branigan, P.C.

(57) ABSTRACT

The present invention relates to a process for continuous metathesis or disproportionation of olefins, comprising at least 2 phases, a reaction phase a) carried out in a zone comprising at least one reactor containing at least one fixed bed of catalyst and a regeneration phase b) carried out in a zone comprising at least one reactor containing at least one fixed bed of catalyst, characterized in that at least one reactor passes from one phase to the other in alternation. In FIG. 1, the feed containing olefins traverses reactor R1 in riser mode. The feed to be treated containing olefins is introduced into reactor R1 via line 1a. In this reactor, the olefins contained in the feed undergo metathesis or disproportionation, then the effluent leaves the circuit via line 11. Simultaneously, reactor R2 is placed in catalyst regeneration phase, the different regeneration gases are introduced into reactor R2 via line 2b and leave this reactor via line 2c. Passage from the operating phase of a reactor to the catalyst regeneration phase thereof is carried out as follows: the reactor for which the catalyst is to be regenerated is isolated from the remainder of the apparatus, the hydrocarbons contained in the reactor are evacuated, then the reactor is purged. Said reactor is then connected to a regeneration loop and undergoes regeneration of its catalyst, and at the end of the regeneration phase, the reactor and the regeneration loop are purged.

18 Claims, 2 Drawing Sheets

ALTERNATED PROCESS FOR OLEFIN METATHESIS

The invention relates to the production of olefins from at least one olefin containing a different number of carbon atoms to that of the desired olefin(s). Processes which can effect this reaction include oligomerisation processes and olefin metathesis or disproportionation reactions. More particularly, the invention relates to metathesis or disproportionation of olefins.

Metathesis or disproportionation of olefins, or a reaction which redistributes alkylidene groups, is of great practical importance, for example for re-equilibration of light olefins from steam cracking or from fluidised bed catalytic cracking (FCC), such as ethylene, propylene and butenes.

Olefin metathesis processes have already been described, in particular in U.S. Pat. 4,795,734, French patent FR-A-2 608 595, U.S. Pat. No. 5,449,852 and FR-A-2 740 056. In FR-A-2 608 595, the reaction is carried out in a moving catalyst bed reactor, and a catalyst regeneration treatment is provided, carried out as follows: a portion of the catalyst is continuously or periodically extracted, the catalyst is sent to an accumulator drum then to a catalyst regeneration apparatus. The regenerated catalyst is returned to the head of the reaction zone.

The present invention provides a process for continuous metathesis or disproportionation of olefins, comprising at least two phases, a reaction phase a) carried out in a zone comprising at least one reactor containing at least one fixed bed of catalyst and a regeneration phase b) carried out in a zone comprising at least one reactor containing at least one fixed bed of catalyst, characterized in that at least one reactor passes from one phase to the other in alternation.

The invention also provides an apparatus for carrying out the process, comprising a reaction zone comprising at least one reactor containing at least one fixed bed of catalyst and a regeneration zone containing at least one reactor containing at least one fixed bed of catalyst.

The apparatus usually comprises 2 to 10 reactors, preferably 2 to 6 reactors and more preferably 4 reactors; when the reaction zone comprises at least 2 reactors, they are mounted in series. The regeneration zone preferably comprises a single reactor. In the reaction phase, the reactors operate in riser mode, but they can also operate in dropper mode or in mixed mode, i.e., a portion of the reactors operate in riser mode, the other reactors operate in dropper mode. Riser mode is preferred, however. In the process, each reactor is alternately in operative mode then in catalyst regeneration mode. Passage from the operative phase of one reactor to its catalyst regeneration phase is carried out as follows: the reactor is isolated from the remainder of the apparatus, the hydrocarbons contained in the reactor are then evacuated and the reactor is purged. The reactor is then connected to a regeneration loop and undergoes catalyst regeneration; at the end of this regeneration phase, the reactor and the regeneration loop are purged by at least one purge treatment, for example using an inert gas or vacuum or successively by at least one purge using an inert gas then vacuum. One or more of the purges can be accomplished by vacuum. After catalyst regeneration, the reactor is replaced in the series of operating reactors, preferably at the end of the series.

The operating reactors can be arranged in series in any order. Preferably, the reactor containing the oldest catalyst is placed at the head (in contact with fresh feed), and the reactor containing freshly regenerated catalyst is placed at the end of the series. This arrangement produces the best performances for feed transformation.

In a preferred implementation of the process of the invention, the reactor to be regenerated is isolated from the operating circuit then the hydrocarbons contained in the reactor to be regenerated are emptied into a receptacle before inserting it into the regeneration loop.

This receptacle can be a surge drum provided for that purpose. After the catalyst regeneration phase, the hydrocarbons contained in this surge drum are sent to the reactor with the regenerated catalyst.

This receptacle can also be a further reactor, in which case the procedure is as follows: the reactor the catalyst of which is to be regenerated is isolated from the operating circuit then the hydrocarbons contained in the reactor are emptied into the reactor which has just been regenerated. The reactor for which the catalyst has just been regenerated is replaced in the operating circuit, preferably at the end of the reactor series, and the emptied reactor is connected to the to regeneration circuit.

Preferably, the hydrocarbons contained in the reactor to be regenerated are recovered in a surge drum.

Advantages of the process of the invention include using a plurality of reactors which are alternately removed from the operating circuit to regenerate the catalyst. Thus if the total catalytic mass (all of the catalysts) is considered, the use of a plurality of reactors enables the unused catalytic mass to be reduced, or more precisely the catalytic mass being regenerated. This operation brings with it a large economic gain, more so since certain of the catalysts used—such as catalysts containing rhenium—are particularly expensive. The use of a plurality of reactors renders the use of catalysts with different compositions and masses possible and also enables elements (furnaces, chillers, pumps, effluent composition monitoring means . . . ) to be inserted depending on the specific requirements of the reaction.

Different types of catalysts are known for use in olefin metathesis or disproportionation which enable either homogeneous type reactors, when the constituent elements are all soluble in the reaction medium, to be used, or heterogeneous type reactions, when at least one of the elements is insoluble in that medium, to be used. The catalysts used in carrying out the process of the invention are solid catalysts preferably containing at least rhenium on a porous support preferably containing alumina. United States patents US-A-4 795 734, French patent FR-A-2 608 595, U.S. Pat. No. 5,449,852 and FR-A-2 740 056 describe catalysts of that type.

Olefins which can react in metathesis or disproportionation catalysed by that type of supported rhenium based catalyst can be linear or branched olefins, preferably linear, with general formula: $R_1R_2C=CR_3R_4$, where $R_1$, $R_2$, $R_3$, $R_4$, which may be identical or different, are hydrogen or a hydrocarbyl radical containing 1 to 20 carbon atoms. The olefins may also be cyclic in structure, the cycle containing 3 to 20 carbon atoms. An olefin may be reacted with itself or with a mixture of a plurality of olefins. The reactions which are of interest to us are preferably metathesis of ethylene and a $C_4$ cut containing 2-butene which produces propylene, and metathesis of ethylene and a $C_5$ cut containing 2-pentene which produces propylene and butenes. The reactions are as follows:

2-butene+ethylene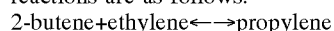propylene 2-pentene+ethylene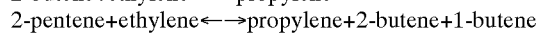propylene+2-butene+1-butene The apparatus of the invention uses 2 to 10 reactors, preferably 2 to 6 reactors and more preferably 4 reactors. The process of the invention continuously converts olefins; regeneration of the catalyst or catalysts of one reactor normally takes 25 to 35 hours.

The olefin-containing feed to be treated is introduced into the first reactor where the olefins undergo a first metathesis or disproportionation step; the used catalyst can also capture impurities which may be contained in the feed. In embodiments where at least two reactors are operating, the effluent leaving the first reactor is introduced into the second reactor where it undergoes a second metathesis or disproportionation step. The effluent thus traverses all of the reactors which are in operation, the olefins undergo metathesis or disproportionation in each reactor, then the effluent is evacuated from the reactor zone.

In each reactor, the reaction conditions are as follows: a temperature of about 0° C. to 100° C., preferably about 30° C. to 60° C., a pressure which is sufficient to keep at least part, if not the majority, of the effluent in liquid form, and an HSV (mass of feed to be treated/mass of catalyst/hour) of about 0.4 to 10 $h^{-1}$, preferably 0.5 to 3 $h^{-1}$. Further, the small temperature rise, about 0.5° C. per reactor, renders the presence of chiller elements between two reactors unnecessary.

Regeneration of the catalyst in one reactor is carried out in a multi-step process, each new regeneration cycle being managed using the procedure explained below. The reactor for which the catalyst is to be regenerated is isolated from the reaction circuit, the hydrocarbons contained in this reactor are evacuated, and the reactor is then purged by a clean dry inert gas then placed in the regeneration circuit. The term "clean gas" as used in the present description means that the amount of impurities in that gas is at most 10000 ppm by volume, and the term "dry gas" as used in the present description means that the amount of water in this gas is at most 1000 ppm by volume. Preferably, a gas containing at most 1000 ppm by volume of impurities and 400 ppm by volume of water is used. The term "impurities" as used in the present description essentially means oxygen. That gas is normally selected from the group formed by nitrogen, carbon dioxide and argon. The scope of the present invention also encompasses a mixture of at least 2 of these gases, but usually nitrogen is used. At the end of the regeneration step, the reactor-regeneration loop system is purged, for example using a vacuum purge.

Before the catalyst is regenerated, the hydrocarbons contained in the reactor the catalyst of which is to be regenerated are evacuated. The hydrocarbon recovery step, which is optional, can be carried out in at least 2 manners: by recovery into a surge drum or by recovery into the reactor which has just been regenerated.

The reactor the catalyst of which is to be regenerated is then isolated from the emptying section and purged with a clean dry gas to eliminate any hydrocarbons which may remain on the catalyst. This gas traverses the reactor in riser or dropper mode, the absolute pressure inside the system is normally about 3 to 60 bar, preferably about 5 to 10 bar.

The reactor is then connected to the regeneration circuit where it undergoes a multi-step treatment.

In a first step, a regeneration gas comprising nitrogen and oxygen is introduced into the apparatus. It is sent to a vessel where it is dried such that its water content at the outlet from that vessel is at least most 1000 ppm by volume, preferably 400 ppm by volume. Then it is introduced into a vessel supplied with air such that the oxygen content of the mixture which leaves that vessel is about 0.2% to 5% by volume. This gas mixture is then heated in a vessel provided with a heating means, then sent to the reactor. The gas mixture traverses the reactor where the catalyst is in its regeneration phase. The gas temperature inside the reactor is normally about 300° C. to 500° C. and the absolute pressure inside the reactor-regeneration loop system is normally about 3 to 60 bars, preferably about 5 to 10 bars. The gas mixture which leaves the reactor contains nitrogen, oxygen and carbon dioxide. A portion of that gas is evacuated from the regeneration circuit, the remainder is recycled. This recycled gas is cooled using any cooling means, for example with a heat exchanger, and dried such that its water content at the outlet from that vessel is at most 1000 ppm by volume, preferably 400 ppm by volume, then introduced again into the regeneration circuit. This first step in the regeneration phase normally takes about 1 to 10 hours, preferably about 1 to 7 hours.

In a second step, a regeneration gas comprising nitrogen and oxygen is introduced into the apparatus. It is sent to a vessel where it is dried such that its water content at the outlet from that vessel is at least most 1000 ppm by volume. preferably 400 ppm by volume. Then it is introduced into a vessel supplied with air such that the oxygen content of the mixture which leaves that vessel is about 1% to 22% by volume, preferably 3% to 10% by volume. The oxygen content of this mixture is preferably higher than that of the gas used in the first regeneration step. This mixture is then heated in a vessel provided with a heating means then the gas is sent to the reactor. The gas mixture traverses the reactor where the catalyst is in its regeneration phase. The temperature inside the reactor is normally about 400° C. to 700° C. and the absolute pressure inside the reactor—regeneration loop system is normally about 3 to 100 bar, preferably about 5 to 10 bar. The regeneration temperature in this step is normally at least equal to that in the first step and is usually higher. The pressure in this step can be higher or lower than that in the first step, and usually the pressures are identical in the two steps. The gas mixture which leaves the reactor contains nitrogen, oxygen and carbon dioxide. A portion of that gas is evacuated from the regeneration circuit, the remainder is recycled. This recycled gas is cooled using any cooling means, for example a heat exchanger, and dried such that its water content at the outlet from that vessel is at most 1000 ppm by volume, preferably 400 ppm by volume. The gas is then re-introduced into the regeneration circuit. This second step in the regeneration phase normally takes about 1 to 10 hours, preferably about 1 to 5 hours.

In a third step, a purge is carried out, for example by vacuum evacuating the reactor- regeneration loop system to evacuate the mixture of gas for which the oxygen content is normally about 1% to 22% by volume. The purge is aimed at reducing the amount of oxygen in the system to a value which is sufficiently low maximise avoidance of the risks inherent in contacting oxygen with hydrocarbons under the operating temperature and pressure conditions of the process. Vacuum purging the reactor—regeneration loop system is carried out at the end of a phase for chilling the reactor contents. The system can be chilled with any chilling means, for example with a heat exchanger. This purge can be carried out using different means for forming a vacuum, in particular a liquid-ring vacuum pump: a sliding pump, a plunger pump, a liquid-ring centrifugal pump, or in a preferred implementation of the process of the invention, a steam ejector, can be used.

This third step is usually carried out in two successive stages.

In a first stage, the system is opened, and the pressure in the system thus returns to atmospheric pressure, the oxygen present is then evacuated from the regeneration loop. In a second stage, the pressure inside the loop is reduced using a vacuum forming means as described above, the interior of the circuit being depressurised to an absolute pressure normally of about 0.2 to 0.3 bars. Then the pressure inside the circuit is increased again with compression means which is internal or external to the apparatus, up to an absolute pressure of about 6 to 8 bars; this compression means can for example, be a reciprocating piston compressor or a centrifugal compressor. The scope of the present invention encompasses more severe depressurisation. Similarly, one or more purges using an inert gas can be carried out between the first and second stages; the pressurisation step is mainly carried out using an inert gas such as one of those cited above or a mixture of at least two of those gases.

A single depressurisation—pressurisation series normally suffices to reach an oxygen content of 1000 ppm by volume in the reactor—loop system. If required, if the oxygen content in the reactor—loop system is to be lower, for example about 5 ppm, at least a second vacuum purge is carried out.

The reactor—regeneration loop system purge can also be carried out using a series of pressurisations to an absolute pressure of about 6 to 8 bars and depressurisations to atmospheric pressure using a clean dry inert gas, usually nitrogen; this can thus have the water contents and impurity contents described above. Normally at least three depressurisation-pressurisation to atmospheric pressure series are required to reach an oxygen content of 1000 ppm by volume in the reactor-loop system. If an oxygen content of 5 ppm by volume is desired in the reactor-loop system, at least 5 depressurisation—pressurisation to atmospheric pressure series normally have to be carried out.

In the process of the invention, purging the reactor—regeneration loop system using vacuum is preferred.

Before reconnecting the reactor to the reaction circuit, the reactor has to be pressurised. The reactor pressure is normally adjusted using the effluent leaving the reaction circuit.

If an apparatus comprising a surge drum is selected, before replacing the reactor the catalyst of which has just been regenerated into the operating circuit, the reactor pressure is adjusted using the reaction effluent then the hydrocarbons temporarily placed in the surge drum are introduced into the reactor.

BRIEF DESCRIPTION OF THE DRAWINGS

FIGS. 1 to 4 illustrate the invention without limiting its scope.

In FIG. 1, the feed containing olefins is treated in a reactor. In this Figure, the effluent traversed the reactor in riser mode.

The olefin-containing feed to be treated is introduced into reactor R1 via line 1a, and the effluent leaves the circuit via line 11 after reaction.

Simultaneously, treatment R2 is placed in the catalyst regeneration phase; the different regeneration gases are introduced into reactor R2 via line 2b and leave this reactor via line 2c.

Figure 2:
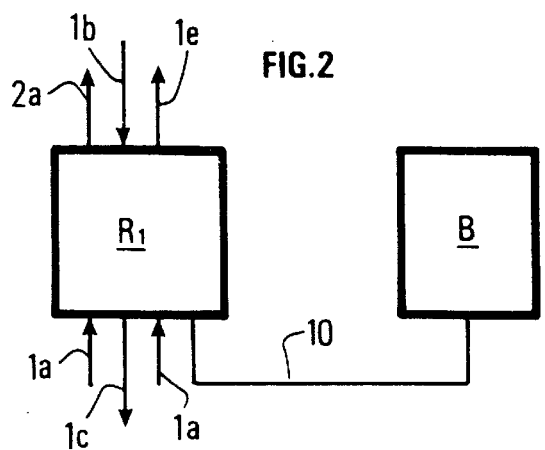
FIG. 2 depicts an apparatus for emptying a reactor prior to regenerating its catalyst.

FIG. 2 shows the apparatus for emptying the reactor before regenerating its catalyst. In this description, reactor 1 has been selected for emptying.

Figure 1:
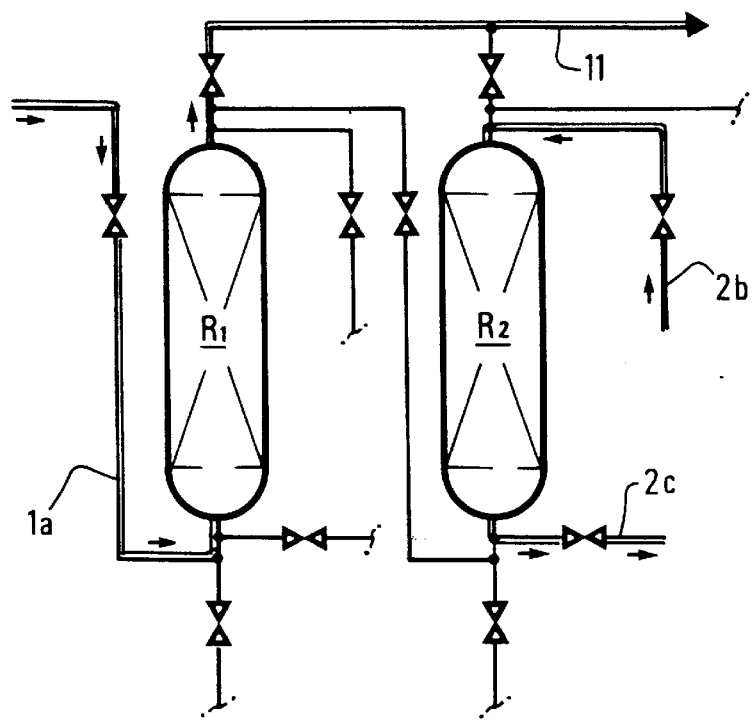
FIG. 1 depicts a reactor $R_1$ treating a feed containing olefins and a reactor $R_2$ being regenerated.

Lines 1a and 2a are respectively admission lines for the feed to be treated and lines for evacuating the effluent produced by reactor R1; these lines form part of the operating apparatus for the reactors detailed above (FIG. 1). Before regenerating the catalyst, the hydrocarbons, mainly in liquid form, are introduced into drum B via line 10.

Reactor R1 is then isolated from the emptying section and a purge is carried out to eliminate any hydrocarbons remaining on the catalyst. The purge gas enters reactor R1 via line 1d and leaves reactor R1 via line 1e.

At the end of the catalyst regeneration phase for reactor R1, the hydrocarbons stored in surge drum B are introduced into reactor R1 via line 10.

Figure 3:
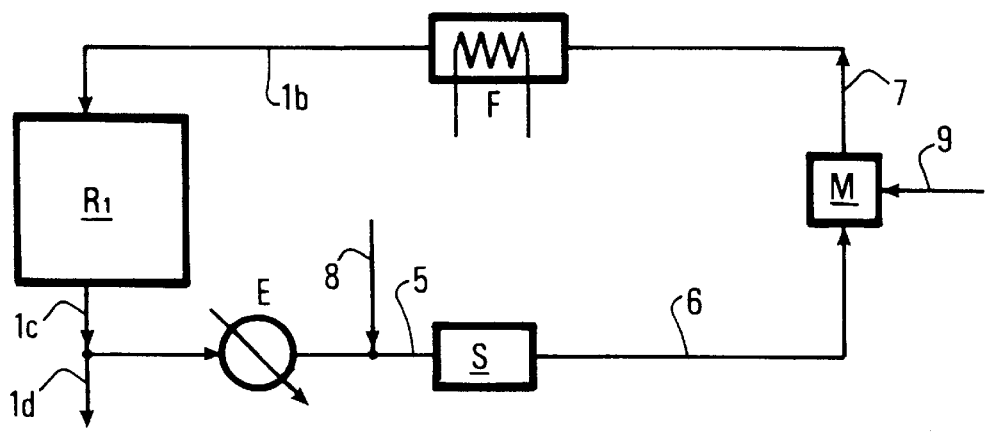
FIG. 3 depicts a catalyst regeneration apparatus.

FIG. 3 shows the catalyst regeneration apparatus. In this description, the regeneration of the catalyst contained in treatment R1 has been selected for presentation.

A regeneration gas is introduced into the apparatus via line 8, and is then sent via line 5 to a vessel S provided with a drying means then it is introduced via line 6 into a vessel M. Vessel M is supplied with air via line 9. The mixture leaves vessel M via line 7 and is sent to a vessel F provided with a heating means then the mixture is sent to reactor R1 via line 1b. The gas mixture traverses reactor R1 and leaves this reactor via line 1c. A portion of this gas is evacuated from the regeneration circuit via line 1d, the remainder is cooled using a heat exchanger E then re-introduced into the regeneration circuit via line 5.

Figure 4:
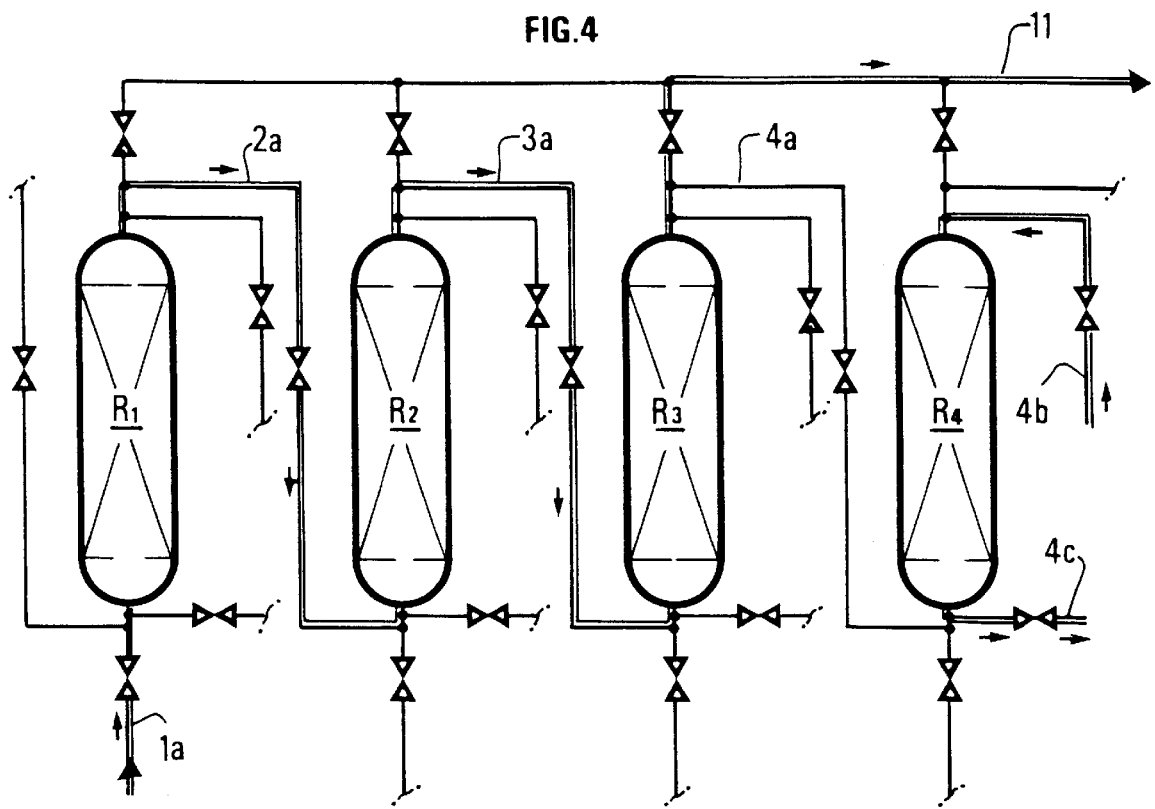
FIG. 4 depicts a preferred embodiment of the apparatus of the invention.

FIG. 4 illustrates a preferred embodiment of the apparatus of the invention. In this embodiment, the reaction zone comprises 3 reactors in series; the effluent successively traverses reactors R1-R2-R3 in that order, in riser mode. The feed to be treated is introduced into reactor R1 via line 1a. This feed traverses reactor R1 then leaves via line 2a before being introduced into reactor R2. This feed traverses reactor R2 then leaves via line 3a before being introduced into reactor R3. This feed traverses reactor R3 then is evacuated from the circuit via line 11.

Simultaneously, reactor R4 is placed in its catalyst regeneration phase; the different regeneration gases are introduced into reactor R4 via line 4b and leave this reactor via line 4c.

The following examples illustrate the invention without limiting its scope.

To facilitate laboratory operation, the following examples were carried out with 2 reactors, one in operation. However, industrial units generally comprise a larger number of operating reactors, and preferably, an apparatus comprising 3 operating reactors and a single regenerating reactor, also a surge drum, are used.

EXAMPLES

The metathesis reactions of the two examples which follow were carried out using an apparatus of the invention comprising two reactors each 5 litres in volume, one in the reaction phase while the other was in the regeneration phase. 1 kg of catalyst was placed in each of these reactors; the catalyst used is described in Example 1 of U.S. Pat. No. 4,795,734. The reactors were connected to a regeneration loop comprising a chiller, a compressor, a water extraction system and a furnace. During the regeneration phase, a vessel provided with an air inlet was introduced into that apparatus, then at the end of the regeneration phase a vacuum pump was introduced to evacuate the system.

Example 1

Metathesis of ethylene and 2-butene

During the reaction phase, a mixture containing butenes, mainly 2-butene was introduced at a rate of 0.9 kg/h into one reactor with pure ethylene (polymerisation quality) at a rate of 0.34 kg/h. The reaction was carried out under the following operating conditions: a temperature of 35° C. and an absolute pressure of 35 bars. The composition of the mixture to be treated is shown in Table 1.

| Compounds | % by weight |
|---|---|
| containing 3 carbon atoms or fewer | 0.5 |
| n-butane + I-butane | 15 |
| isobutene | 0.5 |
| 1-butene | 7.5 |
| 2-butene | 75.5 |
| containing 5 carbon atoms or more | 1 |

The 2-butene conversion was 61% by weight at the reactor outlet. The propylene selectivity was 95% by weight.

After 30 hours of operation, the contents of the reactor which was operating were emptied into the reactor which had just been regenerated and the latter reactor was placed in the operating circuit. The reactor with used catalyst was placed in the regeneration circuit.

During the regeneration phase, which took 30 hours, a hot as containing nitrogen, oxygen and carbon dioxide circulated over the catalyst. At the beginning of the regeneration phase, the oxygen content in the mixture was 0.6% by volume and the clean dry nitrogen content was 99.4% by volume, the temperature inside the reactor was 450° C. and the absolute pressure of the loop-reactor system was 6 bars. This step took 4 hours. Thus firstly, the impurities deposited during the reaction were burned off with an oxygen depleted gas, then the catalyst was calcined in air. This calcining was carried out under the following conditions: the temperature inside the reactor was 550° C. and the absolute pressure in the loop-reactor system was 6 bars. At the end of calcining, which took 2 hours, the oxygen content in the loop-reactor system was 5% by volume, the nitrogen content was 70% by volume, and the carbon dioxide content was 25% by volume. The loop and combustion air circulating therein were chilled using a heat exchanger, then vacuum purging was carried out to reduce the pressure to an absolute pressure of 0.2 bars, and then said loop was filled with nitrogen such that only 0.01% by volume of oxygen remained in the loop. The pressure in the system was then increased to an absolute pressure of 7 bars using clean dry nitrogen containing 50 ppm by volume of water and 300 ppm by volume of impurities.

Catalyst regeneration took 30 hours, this period including the heating and chilling periods. At the end of the 30 hour period, the reactor which contained the catalyst which had just been regenerated was replaced in the reaction zone and the reactor with used catalyst was placed in the regeneration circuit.

Example 2

Metathesis of ethylene and 2-pentene

During the reaction phase, a mixture containing 2-pentene was introduced at a rate of 743 g/h into a reactor with pure ethylene (polymerisation quality) at a rate of 77 g/h. The reaction was carried out under the following operating conditions: a temperature of 35° C. and an absolute pressure of 35 bar. The composition of the mixture to be treated is shown in Table 2.

TABLE 2

| Compounds | % by weight |
|---|---|
| i-pentane + n-pentane | 63.7 |
| 2-methyl-2-butene | 8.3 |
| 1-pentene | 1.6 |
| 2-pentene | 15.8 |
| other olefins containing 5 carbon atoms or more | 10.6 |

The 2-pentene conversion was 65% by weight, that for 2-methyl-2-butene and other olefins containing 5 carbon atoms or more was 80% by weight. The selectivity for olefins containing 3 and 4 carbon atoms was 65% by weight with respect to the total products formed.

After 30 hours of operation, the contents of the reactor which was operating were emptied into the reactor which had just been regenerated and the latter reactor was placed in the operating circuit. The reactor with used catalyst was placed in the regeneration circuit.

This used catalyst regeneration phase was identical in every respect to that described in Example 1. When catalyst regeneration was complete, the reactor containing the regenerated catalyst was replaced in the reaction zone and the other reactor, with used catalyst, was placed in the regeneration zone.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above, and of French priority application 97/15743, filed Dec. 10, 1997, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for continuous metathesis or disproportionation of olefins, comprising:

conducting at least two phases, including reacting the olefins in a reaction phase a) carried out in a zone comprising at least one reactor operating in riser mode containing at least one fixed bed of catalyst, and at least one other reactor in series with the at least one reactor operating in riser mode containing at least one fixed bed of catalyst, and regenerating a catalyst in a regeneration phase b) carried out in the zone comprising at least one reactor containing at least one fixed bed of catalyst, wherein at least one reactor passes from one phase to the other in alternation.

2. A process for continuous metathesis or disproportionation of olefins according to claim 1, in which the regeneration phase is carried out in a zone containing a single reactor.

3. A process for continuous metathesis or disproportionation of olefins according to claim 1, wherein passage from the reaction phase of one reactor to the regeneration phase for its catalyst is accomplished as follows: the reactor for which the catalyst is to be regenerated is isolated from the remainder of the apparatus, the hydrocarbons contained in that reactor are evacuated, then said reactor is purged.

4. A process for continuous metathesis or disproportionation of olefins according to claim 1, wherein a C4 cut containing 2-butene and ethylene is reacted in the reaction phase carried out in the zone comprising the at least one reactor.

5. A process for continuous metathesis or disproportionation of olefins according to claim 1, wherein a C5 cut containing 2-pentene and ethylene is reacted in the reaction phase carried out in the zone comprising the at least one reactor.

6. A process for continuous metathesis or disproportionation of olefins according to claim 1, wherein at least one reactor operates in dropper mode.

7. A process for continuous metathesis or disproportionation of olefins according to claim 1, wherein at least one reactor operates in riser mode, and at least one reactor operates in dropper mode.

8. A process for continuous metathesis or disproportionation of olefins according to claim 1, wherein the catalysts used are solid catalysts containing at least rhenium on a porous alumina-containing support.

9. A process according to claim 1, wherein the reaction phase comprises at least four reactors in series.

10. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst, and
    regenerating a catalyst in a regeneration phase b) carried out in the zone comprising at least one reactor containing at least one fixed bed of catalyst, wherein at least one reactor passes from one phase to the other in alternation, and at least one reactor in the regeneration phase after regeneration and a regeneration loop are purged, and said at least one regenerated reactor then being placed in a series of operating reactors.

11. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst, and
    regenerating a catalyst in a regeneration phase b) carried out in the zone comprising at least one reactor containing at least one fixed bed of catalyst, wherein at least one reactor passes from one phase to the other in alternation, and before regenerating the catalyst in a reactor, said reactor is isolated from a reaction circuit, then the hydrocarbons contained in the reactor are emptied into a further reactor.

12. A process according to claim 11, wherein said further reactor is the reactor for which the catalyst has just been regenerated.

13. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst, and
    regenerating a catalyst in a regeneration phase b) carried out in the zone comprising at least one reactor containing at least one fixed bed of catalyst, wherein at least one reactor passes from one phase to the other in alternation, and before regenerating the catalyst of a reactor, said reactor is isolated from a reaction circuit then the hydrocarbons contained in that reactor are emptied into a surge drum, and after regeneration of its catalyst, the hydrocarbons in the drum are re-introduced into said reactor, the reactor then being placed in a series of operating reactors.

14. A process for continuous metathesis or disproportionation of olefins according to claim 13, wherein the catalyst regeneration phase is terminated by at least one depressurisation step for a reactor-regeneration loop system, the pressure of the system being taken to an absolute pressure of 0.2 to 0.3 bars, followed by at least one pressurisation step for the system.

15. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst, and
    regenerating a catalyst in a regeneration phase b) carried out in the zone comprising at least one reactor containing at least one fixed bed of catalyst, wherein at least one reactor passes from one phase to the other in alternation, and at least one reactor in the regeneration phase after regeneration is placed in a series of operating reactors, at the end of that series.

16. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst, and
    regenerating a catalyst in a regeneration phase b) carried out in the zone comprising at least one reactor containing at least one fixed bed of catalyst, wherein at least one reactor passes from one phase to the other in alternation, and the catalyst regeneration phase is terminated by at least one depressurisation step for a reactor-regeneration loop system, the pressure of the system being taken to an absolute pressure of 0.2 to 0.3 bars, followed by at least one pressurisation step for the system.

17. A process for continuous metathesis or disproportionation of olefins, comprising:
    conducting at least two phases, including reacting the olefins in a reaction phase a) carried out in a zone comprising at least two reactors in series operating in riser mode containing at least one fixed bed of catalyst wherein the catalyst used contains at least rhenium on a porous alumina-containing support; and
    regenerating a catalyst in a regeneration phase b) carried out in the zone comprising at least one reactor containing at least one fixed bed of catalyst wherein at least one reactor after regeneration and a regeneration loop are purged, and said at least one regenerated reactor then being placed in a series of operating reactors, wherein at least one reactor passes from one phase to the other in alternation.

18. A process for continuous metathesis or disproportionation of olefins, comprising:
    conducting at least two phases, including reacting the olefins in a reaction phase a) carried out in a zone comprising at least one reactor operating in riser mode containing at least one fixed bed of catalyst;
    regenerating a catalyst in a regeneration phase b) carried out in the zone comprising at least one reactor containing at least one fixed bed of catalyst, wherein at least one reactor passes from one phase to the other in alternation;

passing a regeneration gas through the reactor in the regeneration phase; and recycling at least a portion of the passed regeneration gas to the regeneration phase; and drying and cooling the portion of the passed recycled regeneration gas.

* * * * *